United States Patent [19]

Arnegger

[11] 4,235,595
[45] Nov. 25, 1980

[54] HANDPIECE WITH CONTINUOUS SHAFT AND BELL ROTOR

[76] Inventor: Richard E. Arnegger, Im Schooren, 8713 Uerikon ZH, Switzerland

[21] Appl. No.: 902,375

[22] Filed: May 3, 1978

[30] Foreign Application Priority Data

May 31, 1977 [CH] Switzerland .................. 6674/77

[51] Int. Cl.$^3$ ................. A61C 1/08; A61F 17/32; A61F 5/04; B23B 5/22
[52] U.S. Cl. .................... 433/131; 279/95; 128/305.1; 128/92 E; 433/114
[58] Field of Search .............. 32/26, 46, 28, DIG. 7; 279/95, 23 A, 41 A; 128/92 E, 305.6; 433/114, 131

[56] References Cited

U.S. PATENT DOCUMENTS

| | | | |
|---|---|---|---|
| 1,538,638 | 5/1925 | Kalberer | 279/41 |
| 2,738,528 | 3/1956 | Fridge, Sr. | 32/28 |
| 2,947,082 | 8/1960 | Epstein | 32/46 |
| 2,985,050 | 5/1961 | Schwacha | 32/46 |
| 3,010,357 | 11/1961 | Hirschowitz | 32/DIG. 7 |
| 3,070,379 | 12/1962 | Misuraca | 279/95 |
| 3,136,059 | 6/1964 | Nelson | 32/28 |
| 3,590,232 | 6/1971 | Sadowski | 240/2 |
| 3,902,248 | 9/1975 | Bareth | 32/26 |
| 4,021,920 | 5/1977 | Kirschner et al. | 32/28 |
| 4,114,276 | 9/1978 | Malata et al. | 32/26 |

Primary Examiner—Louis G. Mancene
Assistant Examiner—Michael J. Foycik, Jr.
Attorney, Agent, or Firm—Donald D. Denton

[57] ABSTRACT

A surgical bone operation instrument that has a straight tube-shaped shaft and arrangement coaxially in relationship to the longitudinal axis of the instrument to form a continuous channel from one end of the instrument to the other including the end parts, which serves for the guidance of materials utilized in the operation of the instrument, and a driving assembly being of a bell-type electrical motor with the stator enclosed within the bell-shaped rotor, the latter having windings of lacquered wire embedded in a plastic material, the windings further being wound to form a hollow cylinder of relatively thin wall thickness to form a part of the bell-shaped rotor, the mechanical structure of the rotor being furthermore reinforced by glass fibers.

11 Claims, 2 Drawing Figures

HANDPIECE WITH CONTINUOUS SHAFT AND BELL ROTOR

BACKGROUND OF THE INVENTION

The present invention relates to a surgical bone operation instrument with a straight shaft, arranged coaxially to the longitudinal axis of the tool, which tool is provided at the side of one end of a hand piece with a working unit and at the side of the other end of the hand piece with a driving assembly.

Such a surgical bone operation instrument, which serves as a drilling or milling apparatus for dentistry work, is already known. It has a longitudinal channel, in which a small tube is extending for the guidance of a cooling means. Each time the driving means is coupled with the drill shaft, the small tube must penetrate a soft, elastic cover, which separates the channel between the drill and the shaft carrying this drill. This is a disadvantage because repeated penetration destroys the cover and it must frequently be replaced. Furthermore, the small tube must have a sharp point, which always presents a possibility of injury and therefore is undesirable; and finally there is always the danger that in penetrating the cover, the small tube will become clogged.

SUMMARY OF THE INVENTION

The surgical bone operation instrument according to this invention avoids the above mentioned disadvantages. It is characterized in that the driving assembly as well as the hand piece each comprises a tube-shaped piece forming a part of said shaft, which shaft pieces are arranged coaxially with respect to the longitudinal axis, one behind the other, and are coupled with their neighboring ends to form over their entire length including their ends a continuous channel, which serves for the guidance of a means utilized for the operation of this instrument.

The instrument according to this invention has the advantage of being universally applicable in the industry, surgery, goldsmith branch and similar fields. If, for example, a drill is used as a working unit, due to the open and straight channel, drills of different lengths may be utilized. In particular, a long drill aternately may be used in its full length or as a short drill by simply being inserted by different amounts of its length into the channel. The channel is also well suited for including a light conductor. Furthermore, the channel can be cleaned very easily. The straight channel allows a perfect sealing thereof and enables the use of a working unit, which will stretch over the whole length of the channel and may even be longer than the channel. Furthermore, it is possible to adjust the length of the instrument so as to vary its length.

BRIEF DESCRIPTION OF THE DRAWINGS

The invention will be explained in further detail with the help of an illustrated embodiment and a drawing of a special construction thereof, in which.

DESCRIPTION OF PREFERRED EMBODIMENTS

Figure 1:
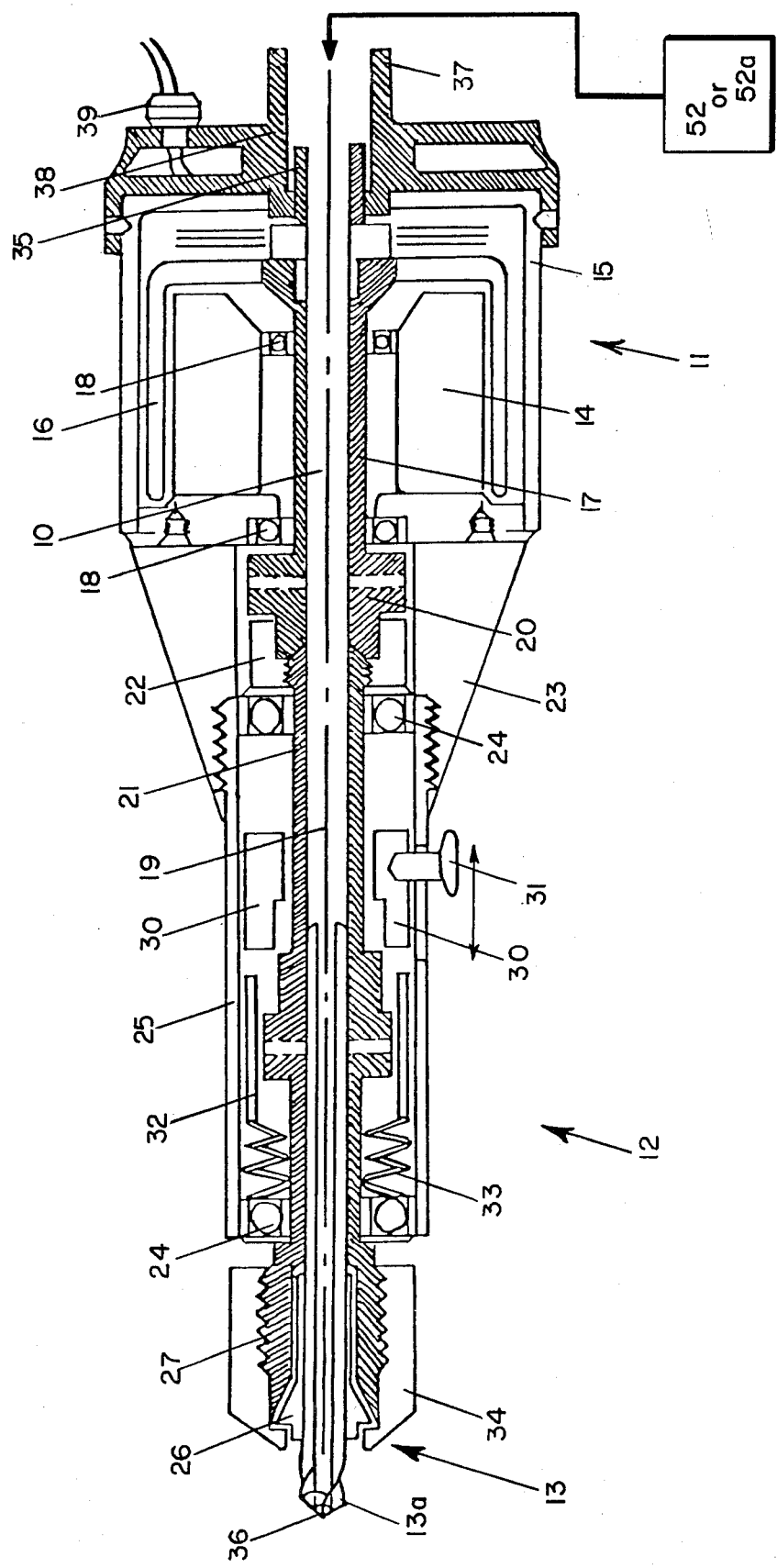
FIG. 1 shows a cross-sectional view of the surgical bone operation instrument according to the invention.

The surgical bone operation instrument shown in the cross-section of FIG. 1 consists mainly of three parts: A driving assembly 11, a hand piece 12, and a working unit 13. The driving means assembly 11 comprises an electric motor, in the example shown a bell-type motor. This motor consists of a fixed permanent magnet or stator 14, which is fixedly connected with a first housing 15. The bell-type motor has a bell-type rotor 16 which is rotatable around the fixed stator 14. The cylindrical part of the rotor 16 comprises windings of lacquered copper wire and the stabilization of this unit is reinforced by glass fibers. In this way it is possible to make the bell-type rotor 16 very thin and still to make the motor very strong. In addition to this, it is possible to make the motor heat resistant.

The bell-type rotor 16 is fixed to a shaft piece 17. The latter is rotatably mounted in a ball bearing means 18. On one end of the shaft piece 17 there is a first coupling part 20, which is coupled with a second coupling part 22, affixed to a shaft piece 21. The coupling parts 20, 22 are shielded from the outside by a conical flange or shield 23. The shaft piece 21 is rotatably mounted in a second ball bearing means 24 and is placed in the interior of housing part 25. In connecting the conical shield 23 with the first and second housing parts 15 and 25, the coupling parts 20, 22 will be joined together and coupled to one another. Together with other parts, the parts 21, 24, and 25 form the hand piece 12 of the instrument.

In the working unit 13, in the case of the example shown, a drill 13a can be attached to the hand piece 12. The diameter or thickness of the drill, for this purpose, is adjusted to the size of the bore of the shaft piece 21, formed by a hollow cylinder. An internally threaded tension sleeve 34, a conical link or collet 26 through which the drill shank can be adjustably positioned, and an organ or externally threaded collet 27 provided mating screw threads can, by turning the tension sleeve 34, clamp the drill in the shaft piece 21. A lengthwise movable coupling part 30 with a knob 31, a cylindrical distance tube 32 and a spring or biasing means 33 serve for the necessary fixation of the shaft piece 21 when exchanging the working unit 13 (see FIG. 1).

According to the present invention, the shaft piece 17 of the bell-type motor as well as the shaft piece 21 of the hand piece 12 are provided with a longitudinal bore. The shaft pieces 17 and 21 are placed behind one another and arranged coaxially to the longitudinal axis designated as 19 of the instrument and form a channel 10 extending over the entire length of the shaft pieces including the end parts, which channel serves for the guidance of a means utilized for the operation of the working unit.

The example as described and set forth in the drawings shows an instrument with a very great number of possible applications, of which the following examples shall be brought to notice:

If the coupling consisting of parts 21, 22 is securely sealed and the working unit 13 also is provided with a longitudinal bore, a liquid or a gas, serving for instance for cooling purposes, can be fed through the channel 10, by inserting this liquid or gas at end 35 on the side of the motor so that at the outlet at the end 36 the working unit as well as the material to be worked will be cooled by the flowing liquid or gas.

Another embodiment would be such that at the end 36 there can be made an inlet, so that the material is sucked from the working point into the inlet 36 and is removed through the channel 10. The pipe socket 37 serves as a convenient connecting means for a hose means 50 delivering a cooling medium from a cooling medium source 52 or for being connected to a suction pump 52a if the end 36 is to be an inlet instead of an outlet.

In a further embodiment a light conductor or an optical wave guide is provided in the channel 10 which is formed by the shaft pieces 17, 21 and the drill 13a. This optical wave guide can be built by vaporizing or metallizing the wall of the channel, or the optical wave guide can be built by a tube or a rod of glass or a suitable plastic material such as "Lucite" or "Plexiglas", which extends from end 35 to the immediate vicinity of end 36. Such a tube or rod will be carried at least by the inner wall of the working unit 13 and the shaft piece 17. It is also possible to insert into each of the bores of the shaft pieces 17 and 21 as well as the bore of the working unit 13 a separate tube or rod built of glass serving as light conductor. In this embodiment, to keep the loss of light as small as possible, the connecting ends of the different cylinders must be joined at their adjacent ends in such a way that light reflections are at a minimum at the connecting points. It is possible that the end of the inserted light conductor at the end of the drill 13a located inside the shaft piece 21 (in the drawing on the right-hand side) would be widened or the optical wave guide of the shaft piece 21 has a conically tapered end, which fits the end of the light conductor of the drill 13a.

The light transmitted through the light conductor or optical wave guide serves for the illumination of the working area. It serves particularly as a means to accurately position and guide the working unit 13 carrying drill 13a. When using the light ray for central positioning and guiding of the working unit, the latter is preferably built as a tool arranged eccentrically in relation to the axis 19.

In a still further embodiment, the channel 10, which is formed by the shaft pieces 17, 21, serves to guide a wire forming the working unit, which operates as a drill or in a hammering fashion. This embodiment has the advantage that the wire, after loosening the clamp 34, 26, can be pushed forward by an end thereof projecting out of the rear end 35 or in that the wire is drawn at its front end.

To produce a straight channel 10, which is open over its whole length, a driving device 11 permitting such a structure, for example a motor with a fixed central part, is necessary. This requirement is fulfilled in an ideal manner by a bell-type motor, so that an embodiment with such a motor is particularly advantageous for the present invention. A bell-type motor also has the advantage that the bell-type rotor 16 can be built in such a manner of windings of lacquered copper wire that the windings form a relatively thin cylinder surface. Consequently, the motor itself is of relatively light weight. If the cylinder surface formed by copper wires is reinforced by glass fibers, the bell-type rotor 16 will not deform itself even if running at high speed. By an appropriate choice of the plastic material used for the assembly of the rotor, a constant coefficient of expansion up to over 100° C. and a rotor which will be water repellent can be obtained.

The aforesaid embodiment of the bell-type motor has the additional advantage that it permits a construction of the surgical bone operation instrument in which all parts will endure temperatures of more than 130° C. Therefore, this instrument is well suited for surgical use in which quick sterilization (autoclavation) of more than 130° C. is required.

It will be appreciated that instead of an electrical motor, a driving assembly comprising a water, air or gas turbine can be used. These units also have the advantage of excellent durability at the temperature required for autoclavation.

At the end of the driving assembly 11 remote from the handpiece 12 a terminal cover 38 is provided. This cover 38 has an opening formed by a tube socket 37 which is coaxial in relation to the axis 19 of the instrument. A connecting member 39 which serves as a plug for the electrical current from an electrical source means for driving the bell-type motor 14, 16 is eccentrically arranged with respect to the axis 19 in the cover 38.

Figure 2:
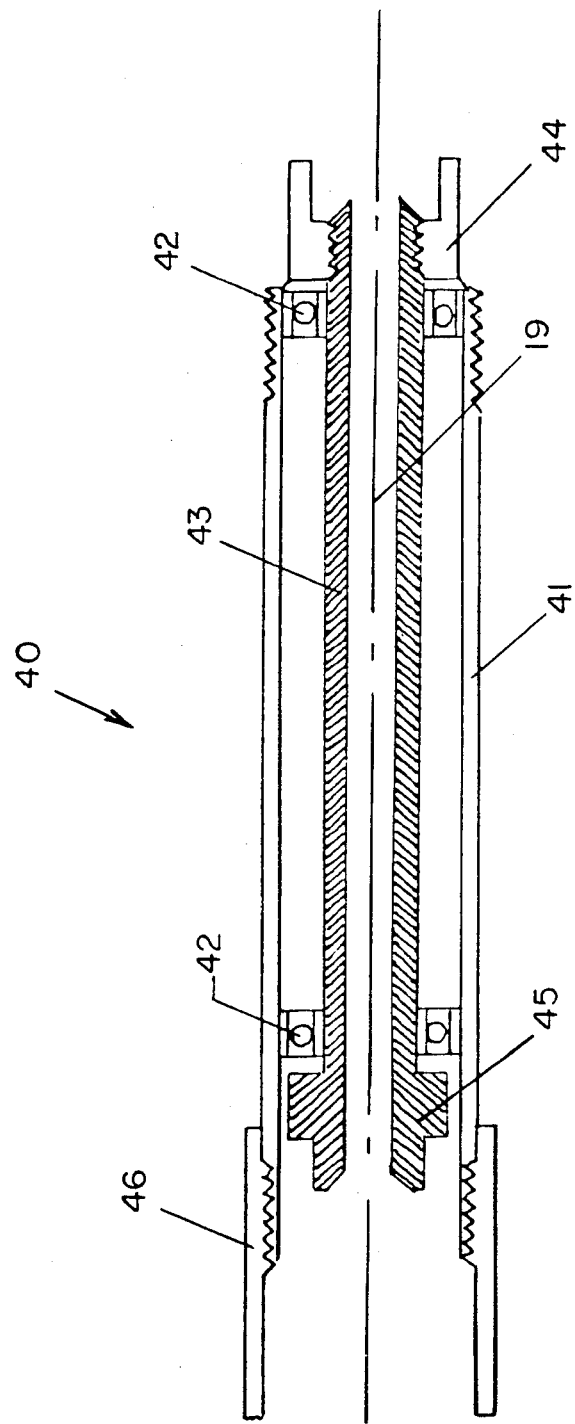
FIG. 2 shows a cross-sectional view of a special form of a constructive outlay.

The instrument according to the present invention can be changed in length easily and can therefore also be used in certain cases of difficult accessibility. In such a form of construction there is arranged a lengthening piece in between the driving assembly 11 and the hand piece 12. FIG. 2 shows an example of such a lengthening piece 40. This lengthening piece comprises a housing part 41 with two bearing means 42, rotatably carrying a shaft piece 43. The latter has at one end a first coupling part 44 and at the other end a second coupling part 45.

To place the lengthening piece 40 between the driving assembly 11 and the hand piece 12, the right side of the coupling piece 40, as seen in FIG. 2, is screwed onto the conical flange or shield mounting 23 of FIG. 1, thereby coupling the coupling parts 20 and 44 with one another. A tube 46 has an internal screw thread and is screwed onto the lengthening part 40 at its left-hand side, as seen in FIG. 2. Also, the hand piece 12 is screwed onto the tube 46 thereby coupling the coupling part 22 shown in FIG. 1 to coupling part 45. The bore of the shaft piece 43 forms an intermediate piece of the channel 10, formed by the driving assembly 11 and the hand piece 12, so that one continuous channel is present.

It will be appreciated that it is naturally possible to utilize more than one lengthening piece 40. It is of advantage if the shaft piece of each lengthening piece on each of its ends is supported in a bearing and if the length of each individual lengthening piece 40 is about equal to the length of the hand piece 12. The described manner of lengthening the hand tool is of great value for industrial use and for special cases in the medical field.

The embodiment of the motor as shown in FIG. 1 has a very high starting torque power. Furthermore, by providing a pole reverse switch, the sense of rotation of the motor can be freely chosen, enabling the drilling of thread windings into solid material.

It will be appreciated that by providing means for the reversing of the poles of the drive energy supply to the drive assembly, the direction of rotation of the drive assembly can be selectively controlled.

What is claimed is:

1. A surgical bone operation instrument with a straight shaft arranged coaxially in relation to the longitudinal axis of the instrument, which instrument is provided at the one end of a hand piece with a working unit and at the other end of the hand piece with a driving assembly, the driving assembly and the hand piece each having a tube-shaped shaft piece forming a part of said shaft, which shaft pieces are arranged coaxially with respect to the longitudinal axis of the tool and behind one another, and with their neighboring ends are coupled together, forming over their entire length including their ends a continuous channel which serves for the guidance of a means utilized in the operation of the instrument, said driving assembly being a bell-type electrical motor with the stator enclosed within the bell-shaped rotor, the latter comprising windings of lacquered wire embedded in a plastic material, said windings further being wound to form a hollow cylinder of relatively thin wall thickness to form a part of the bell-shaped rotor, the mechanical structure thereof being furthermore reinforced by glass fibers.

2. The instrument according to claim 1, in which the stator of the electrical motor comprises a permanent magnet provided with a central bore to receive the tube-shaped shaft piece.

3. The instrument according to claim 1 in which the bell-shaped rotor is comprised of a plastic material of which the coefficient of expansion remains substantially constant up to at least 100° C. and which is water repellent.

4. The instrument according to claim 1 in which the motor is a direct current motor and the direction of rotation of the motor is dependent on the polarization (or direction) of the current applied thereto, and there is provided a means to selectively reverse the polarization of the current applied to the motor.

5. The instrument according to claim 1 in which each one of the tube-like shaft pieces is arranged inside a stationary housing and each one is fixed with a coupling part and, when the housings are fastened together, the coupling of the two shaft pieces is effected by the two coupling parts being joined together.

6. The instrument according to claim 1 in which inside the channel there is arranged a light conductor means.

7. The instrument according to claim 1 in which inside the channel there is arranged an optical wave guide means.

8. The instrument according to claim 6 in which the light conductor means comprises a tube-like cylinder.

9. The instrument according to claim 6 in which the light conductor means comprises a full cylinder of light conducting material.

10. The instrument according to claim 1 in which the driving device on its remote end, in relation to the hand piece, is supplied with a terminal cover which has an opening which is arranged coaxially with respect to the longitudinal axis of the tool and which carries a connection member for supplying driving energy from a source means for the driving assembly, which connecting member is arranged eccentrically in relation to said longitudinal axis.

11. The instrument according to claim 1 in which in between the hand piece and the driving assembly there is placed at least one lengthening piece which is coupled with the driving assembly as well as with the hand piece and which also comprises a tube-like shaft piece, which is arranged with respect to the longitudinal axis and in between the shaft pieces of the driving assembly and the hand piece and which also serves for the guidance of a means utilized for the operation of the tool.

* * * * *